US011536717B2

(12) United States Patent
Takahashi et al.

(10) Patent No.: US 11,536,717 B2
(45) Date of Patent: Dec. 27, 2022

(54) METHOD OF AGGLUTINATION IMMUNOASSAY (71) Applicants: SEKISUI MEDICAL CO., LTD., Tokyo (JP); HITACHI HIGH-TECHNOLOGIES CORPORATION, Tokyo (JP)

(72) Inventors: Hiroshi Takahashi, Tokyo (JP); Tadaaki Yoshida, Tokyo (JP); Yoshimasa Banba, Tokyo (JP); Yuki Takahashi, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 103 days.

(21) Appl. No.: 16/256,732

(22) Filed: Jan. 24, 2019

(65) Prior Publication Data
US 2019/0154674 A1 May 23, 2019

Related U.S. Application Data (63) Continuation of application No. 14/894,207, filed as application No. PCT/JP2014/064659 on Jun. 2, 2014, now abandoned.

(30) Foreign Application Priority Data

May 31, 2013 (JP) .................................. 2013-115756

(51) Int. Cl.
*G01N 33/543* (2006.01)
*G01N 21/47* (2006.01)
*G01N 21/31* (2006.01)
*G01N 21/59* (2006.01)
*G01N 21/83* (2006.01)
G01N 21/17 (2006.01)

(52) U.S. Cl.
CPC ....... *G01N 33/54313* (2013.01); *G01N 21/31* (2013.01); *G01N 21/47* (2013.01); *G01N 21/59* (2013.01); *G01N 21/83* (2013.01); G01N 2021/1734 (2013.01); G01N 2333/705 (2013.01)

(58) Field of Classification Search
CPC .......... G01N 2021/1734; G01N 21/31; G01N 21/47; G01N 21/59; G01N 21/83; G01N 2333/705; G01N 33/54313
See application file for complete search history.

(56) References Cited

U.S. PATENT DOCUMENTS

| 6,750,063 | B1 | 6/2004 | Kawamura |
| 6,969,612 | B2 | 11/2005 | Kawamura |
| 9,664,678 | B2 | 5/2017 | Yogi et al. |
| 2001/0006819 | A1 | 7/2001 | Kawamura |
| 2002/0168784 | A1 | 11/2002 | Sundrehagen |
| 2004/0018629 | A1 | 1/2004 | Kawate |
| 2012/0252005 | A1 | 10/2012 | Chiang et al. |
| 2014/0140890 | A1 | 5/2014 | Adachi et al. |
| 2014/0220705 | A1 | 8/2014 | Yogi |
| 2019/0226988 | A1* | 7/2019 | Iwamoto ................ G01N 21/64 |

FOREIGN PATENT DOCUMENTS

| CN | 101907628 A | 12/2010 |
| CN | 202196011 U | 4/2012 |
| EP | 0 822 412 A1 | 2/1998 |
| JP | 8-43393 A | 2/1996 |
| JP | 11-108929 A | 4/1999 |
| JP | 2001-194308 A | 7/2001 |
| JP | 2001-249134 A | 9/2001 |
| JP | 2001-289853 A | 10/2001 |
| JP | 2008-8794 A | 1/2008 |
| JP | 2008-298505 A | 12/2008 |

(Continued)

OTHER PUBLICATIONS

English translation of International Preliminary Report on Patentability and Written Opinion dated Dec. 10, 2015, in PCT International Application No. PCT/JP2014/064659.
Extended European Search Report, dated Jan. 16, 2017, for European Application No. 14804366.4.
International Search Report, issued in PCT/JP2014/064659, dated Jul. 1, 2014.
Japanese Notice of opposition to patent for Japanese Patent No. 6675104, dated Oct. 1, 2020, with an English translation.
Tsubota, "Measurement Method Using Latex Agglutination Reaction," Recent Advances in Clinical Chemical Analysis, Aug. 1984, 19 pages total, with an English translation.

(Continued)

*Primary Examiner* — Galina M. Yakovleva
(74) *Attorney, Agent, or Firm* — Birch, Stewart, Kolasch & Birch, LLP (57) ABSTRACT

The present invention provides a particle enhanced agglutination immunoassay including the steps of: mixing a sample solution containing an analyte with a solution containing insoluble carrier particles carrying a binding partner or binding partners for the analyte to prepare a mixed solution; determining a variation (i) in intensity of light scattered from the mixed solution based on a difference in intensity of scattered light between first and second time points; determining a variation (ii) in absorbance of the mixed solution based on a difference in absorbance between third and fourth time points; and correlating the determined variation (i) in intensity of scattered light and the determined variation (ii) in absorbance with an amount of the analyte present in the sample using a calibration curve plotted based on the variation in intensity of scattered light and a calibration curve plotted based on the variation in absorbance. The present invention employs measurements of the intensity of scattered light and the absorbance in combination for a single assay, and thus provides a particle enhanced agglutination immunoassay which achieves higher sensitivity and a wider dynamic range than conventional assays.

7 Claims, 3 Drawing Sheets

(56) References Cited

FOREIGN PATENT DOCUMENTS

| JP | 2011-257243 A | | 12/2011 |
|----|---------------|---|---------|
| JP | 2012-78181 A | | 4/2012 |
| JP | 2012-237691 A | | 12/2012 |
| JP | 2013-64705 A | | 4/2013 |
| JP | 2013-68442 A | | 4/2013 |
| WO | WO 00/06991 A2 | | 2/2000 |
| WO | WO 2013/042524 A1 | * | 3/2013 |

OTHER PUBLICATIONS

Korean Office Action for Korean Application No. 10-2015-7036625, dated Feb. 26. 2021, with English translation.
Korean Office Action dated Aug. 19, 2020 for Application No. 10-2015-7036625 with an English translation.
Office Action dated Jan. 26. 2021, in Japanese Patent Application No. 2018-226654.
Japanese Office Action, dated Nov. 6, 2019, for Japanese Application No. 2018-226654, with an English machine translation.
Japanese Argument in Opposition for Japanese Application No. 2020-700751, dated Jun. 14, 2021, with English translation.
Chinese Office Action and Search Report for Chinese Application No. 201480042591.7, dated Nov. 17, 2017, with English translation of the Office Action.
Chinese Office Action and Search Report for Chinese Application No. 201480042591.7, dated Sep. 18, 2018, with English translation of the Office Action.
Chinese Office Action and Search Report for Chinese Application No. 201910108604.0, dated Sep. 30, 2021, with English translation.
Chinese Office Action and Search Report for Chinese Application No. 201910108604.0, dated Aug. 16, 2022, with an English translation of the Chinese Office Action.

* cited by examiner

(A) Results under conditions of measurement of absorbance 1

[FIG.2B]

(B) Results under conditions of measurement of absorbance 2

[FIG.3]

METHOD OF AGGLUTINATION IMMUNOASSAY

This application is a Continuation of copending application Ser. No. 14/894,207 filed on Mar. 15, 2016, which is the U.S. National Phase of PCT/JP2014/064659, filed Jun. 2, 2014, and which claims priority under 35 U.S.C. § 119(a) to Application No. 2013-115756 filed in Japan, on May 31, 2013, the entire contents of all of which are expressly incorporated by reference into the present application.

TECHNICAL FIELD

The present invention relates to an agglutination immunoassay, more particularly to a particle enhanced agglutination immunoassay involving the measurement of intensity of scattered light and the measurement of absorbance.

BACKGROUND ART

In the current field of clinical reagents, many reagents are practically used for use in particle enhanced agglutination immunoassay. Particle enhanced agglutination immunoassay is a method for determining an analyte with carrier particles carrying a binding partner or binding partners for the analyte. Immunoassays using such reagents are performed with an automated analyzer, which can obtain results within a short time through a simple operation. The optical measurement performed with such an automated analyzer determines the intensity of scattered light or the absorbance, either of which is independently performed in a single immunoassay.

Immunoassays based on the measurement of intensity of scattered light provide high sensitivity, but have a very narrow dynamic range. Due to their narrow dynamic range, repeated sample dilutions and remeasurements are required until the concentration of the analyte become within the measurement range of the assay system. As a result, such immunoassays take a lot of time for reporting the assay results.

Meanwhile, it is well known to the persons skilled in the art that immunoassays based on the measurement of absorbance have a somewhat wider dynamic range in comparison with that in immunoassays based on the measurement of intensity of scattered light, but are inferior in the accuracy of measurement of the low concentration analytes.

Some techniques for solving such problems in particle enhanced agglutination immunoassays are known. For example, Patent Document 1 discloses an assay method which aims at providing higher sensitivity and wider dynamic range by performing measurements at different wavelengths.

The reagents for particle enhanced agglutination immunoassay disclosed in Patent Documents 2 and 3 aim at providing a wider dynamic range by using two carrier particles of different sizes in combination with antibodies which have different reactivities to an analyte of interest.

RELATED ART

Patent Documents

Patent Document 1: Japanese Patent Application Laid-Open Publication No. H08-043393
Patent Document 2: Japanese Patent Application Laid-Open Publication No. H11-108929
Patent Document 3: Japanese Patent Application Laid-Open Publication No. 2001-289853

SUMMARY OF INVENTION

The essence of the technique disclosed in Patent Document 1 is to control the absolute value of the signal: At a low concentration of an analyte, the measurement is performed at a short wavelength which provides a strong signal, and at a high concentration of the analyte, the measurement is performed at a long wavelength which prevents the signal from exceeding the upper limit of detection of the analyzer. Unfortunately, as known to those skilled in the art, the turbidity of a microparticle solution depends on the wavelength, and a signal is weaker at a longer wavelength. The technique disclosed in Patent Document 1 merely controls the signal intensity for a certain optical change by selecting the wavelength, so that the signal can be detected by the analyzer, and is not expected to have a dramatic improvement effect to compensate the drawbacks of limited accuracy and dynamic range in particle enhanced agglutination immunoassays.

The smaller particles contained in the reagents for assay disclosed in Patent Documents 2 and 3 undergo small optical changes associated with aggregation and can be formulated in large amounts, and the antibody with lower reactivity contained in such reagents has low aggregation ability. Both techniques are therefore expected to have an effect of expanding the dynamic range. Unfortunately, the reductions in optical changes and aggregation ability resulting from use of smaller particles and use of antibodies with lower reactivity are obstacles for achieving expected properties related to sensitivity of the assay.

As described above, it is difficult to achieve both increased sensitivity and an expended dynamic range, and no particle enhanced agglutination immunoassay has been practically used which achieves both of these improvements.

The present inventors have conceived to combine measurements of the intensity of scattered light and the absorbance for a single assay in particle enhanced agglutination immunoassay to achieve an assay with increased sensitivity and an expanded dynamic range, and have demonstrated the potential of such an immunoassay.

Some conventional analyzers can measure the intensity of scattered light and the absorbance substantially at the same time, as that disclosed in Japanese Patent Application Laid-Open Publication No. 2001-141654, for example. Such analyzers merely aim at practicing the two different analytical methods with a single analyzer: the intensity of scattered light is measured for agglutination immunoassay, and the absorbance is measured for spectrophotometry to determine spectral changes associated with enzymatic or chemical reactions. Conventional documents neither describe nor suggest, and no one has conceived of, a particle enhanced agglutination immunoassay including both measurements in combination in a single assay.

One of causes which have hindered the conception of such a method is the great dependence of the sensitivity and dynamic range of particle enhanced agglutination immunoassay on the composition of a reagent used for assay. A degree of aggregation caused by a reaction between an analyte and carrier particles carrying a binding partner or binding partners for the analyte for a certain time was controlled by selecting main components of a reagent for assay, that is, by selecting the type or amount of the binding partner, or the size of the carrier particles, as described above. Specifically, use of larger particles and a binding partner with higher reactivity results in increased sensitivity, and use of smaller particles and a binding partner with lower reactivity results in a wider dynamic range. Based on the above, persons skilled in the art have concentrated their efforts for increased sensitivity and expanded dynamic range in particle enhanced agglutination immunoassay on design of reagents for assay.

Unfortunately, it is difficult to achieve both increased sensitivity and expanded dynamic range at the same time, as described above, and those skilled in the art often have to design reagents for assay so as to improve either sensitivity or dynamic range while sacrificing the performance of the other, taking the balance between these two characteristics into consideration and depending on a target value of the analyte in a sample. Thus, their efforts concentrated on the design of reagents for assay with various compositions have been inadequate for improvements in both of the two performances to significantly solve that problem.

An object of the present invention is to provide a simpler particle enhanced agglutination immunoassay with higher sensitivity and wider dynamic range than conventional techniques, by combining measurement of the intensity of scattered light to achieve high sensitivity and measurement of the absorbance under analytical conditions specific for expansion of dynamic range in a single assay.

Solution to Problem

The inventors, who have made extensive studies, have arrived at a particle enhanced agglutination immunoassay including both measurement of the intensity of scattered light and measurement of the absorbance in a single assay performed with a reagent which is designed to provide high sensitivity in measurement of the intensity of scattered light but limits a dynamic range. The method includes determining a variation in absorbance between two time points, wherein the time period between the two time points is shorter than the time period for which a variation in intensity of scattered light is determined. As a result, the inventors have successfully plotted calibration curves which substantially cover both low and high concentration ranges of analyte in a single assay, and have accomplished a particle enhanced agglutination immunoassay which includes both measurement of the intensity of scattered light and measurement of the absorbance in combination and which achieves high sensitivity and a wide dynamic range.

The present invention provides the following aspects:

Aspect [1]. A particle enhanced agglutination immunoassay including the steps of: mixing a sample solution containing an analyte with a solution containing insoluble carrier particles carrying a binding partner or binding partners for the analyte to prepare a mixed solution; determining a variation (i) in intensity of light scattered from the mixed solution based on a difference in intensity of scattered light between first and second time points; determining a variation (ii) in absorbance of the mixed solution based on a difference in absorbance between third and fourth time points; and correlating the determined variation (i) in intensity of scattered light and the determined variation (ii) in absorbance with an amount of the analyte present in the sample using a calibration curve plotted based on the variation in intensity of scattered light and a calibration curve plotted based on the variation in absorbance.

Aspect [2]. The immunoassay according to Aspect [1], wherein the first, second, third, and fourth time points are respectively selected between 0 and 1000 seconds after the start of preparation of the mixed solution.

Aspect [3]. The immunoassay according to Aspect [1] or [2], wherein the time period which is defined by the third and fourth time points and for which the variation (ii) is determined is shorter than the time period which is defined by the first and second time points and for which the variation (i) is determined.

Aspect [4]. The immunoassay according to any one of Aspects [1] to [3], wherein the variations (i) and (ii) are determined at the same wavelength.

Aspect [5]. The immunoassay according to any one of Aspects [1] to [3], wherein the variation (ii) in absorbance is determined at a wavelength within a range of ±25% of a wavelength at which the variation (i) in intensity of scattered light is determined.

Aspect [6]. The immunoassay according to Aspect [5], wherein the variation (ii) in absorbance is determined at two wavelengths consisting of main and sub-wavelengths which are shorter and longer, respectively, than the wavelength at which the variation (i) in intensity of scattered light is determined.

Aspect [7]. The immunoassay according to any one of Aspects [1] to [6], wherein the variations (i) and (ii) are determined at a wavelength within the range of from 550 to 900 nm.

Effects of Invention

The present invention provides a particle enhanced agglutination immunoassay which provides higher sensitivity and a wider dynamic range than conventional assays and which reduces efforts and costs required for designing reagents for use in particle enhanced agglutination immunoassay.

DESCRIPTION OF EMBODIMENT

The present invention will now be described with reference to embodiments, which should not be construed to limit the present invention.

In one embodiment, the particle enhanced agglutination immunoassay includes the steps of:

mixing a sample solution containing an analyte with a solution containing insoluble carrier particles carrying a binding partner or binding partners for the analyte to prepare a mixed solution;

determining a variation (i) in intensity of light scattered from the mixed solution based on a difference in intensity of scattered light between first and second time points;

determining a variation (ii) in absorbance of the mixed solution based on a difference in absorbance between third and fourth time points; and correlating the determined variation (i) in intensity of scattered light and the determined variation (ii) in absorbance with an amount of the analyte present in the sample using a calibration curve plotted based on the variation in intensity of scattered light and a calibration curve plotted based on the variation in absorbance.

The method including such steps according to the embodiment of the present invention allows to plot calibration curves which substantially cover both low and high concentration ranges of analyte, and achieves high sensitivity and a wide dynamic range in particle enhanced agglutination immunoassay.

In a preferred embodiment, the first, second, third, and fourth time points are respectively selected between 0 and 1000 seconds after the start of preparation of the mixed solution. Selecting the time points within this range provides both desired sensitivity and dynamic range for the immunoassay, and also allows a high degree of freedom in design of a reagent for assay.

The variation (i) in intensity of scattered light and the variation (ii) in absorbance are preferably determined at the same wavelength, and preferably within the range of from 550 to 900 nm.

The particle enhanced agglutination immunoassay according to embodiments of the present invention will now be described in detail with explanation on elements included in the embodiments, including insoluble carrier particles and analyte.

As used herein, the term "single assay" refers to a series of reactions and measurements performed in a single reaction cuvette. For example, "a single assay" in an immunoassay performed with an automated analyzer includes the following steps which are carried out in a single reaction cuvette: mixing a first reagent solution with a sample; subsequently adding and mixing a second reagent solution (i.e. solution containing insoluble carrier particles carrying a binding partner or binding partners for the analyte); determining a variation in intensity of scattered light; and determining a variation in absorbance.

As used herein, the term "sample solution containing an analyte" includes a sample solution mixed or diluted with a first reagent solution (buffer solution) as described above.

As used herein, the term "intensity of scattered light" is also interchangeably referred to as "scattered light intensity".

(Insoluble Carrier Particles)

The insoluble carrier used in the particle enhanced agglutination immunoassay of the present invention may be any material that is applicable as a component of a reagent for assay. Specific examples of the insoluble carrier include latex, colloidal metal, silica, and carbon. The insoluble carrier particles may have any average particle size appropriately selected from within the range of from 0.05 to 1 μm. In a preferred embodiment, the reagent for use in the particle enhanced agglutination immunoassay of the present invention contains carrier particles having an average particle size which is smaller than the wavelength of the light irradiated during the measurement of the intensity of scattered light with a difference of 250 to 450 nm, specifically 300 to 450 nm. For example, if the light irradiated during the measurement of the intensity of scattered light has a wavelength of 700 nm, the insoluble carrier particles preferably have an average particle size of 250 nm to 400 nm. The average particle size of the insoluble carrier particles can be determined by a general method with a particle analyzer or a transmission electron microscope, for example.

(Sample)

The particle enhanced agglutination immunoassay of the present invention is applicable for determination of various types of biological samples, including, but not limited to, body fluids such as blood, serum, plasma, and urine, for example.

(Analyte)

The analyte to be determined in the particle enhanced agglutination immunoassay of the present invention can be any molecule that can be theoretically determined by particle enhanced agglutination immunoassay, such as proteins, peptides, amino acids, lipids, sugars, nucleic acids, and haptens. Examples of the analyte include CRP (C-reactive protein), Lp (a) (lipoprotein (a)), MMP3 (matrix metalloproteinase 3), anti-CCP (anti-cyclic citrullinated peptide) antibody, antiphospholipid antibody, anti-syphilis antigen antibody, RPR, type IV collagen, PSA, AFP, CEA, BNP (brain natriuretic peptide), NT-proBNP, insulin, microalbumin, cystatin C, RF (rheumatoid factor), CA-RF, KL-6, PIVKA-II, FDP, D-dimer, SF (soluble fibrin), TAT (thrombin-antithrombin III complex), PIC, PAI, factor XIII, pepsinogen I, pepsinogen II, phenytoin, phenobarbital, carbamazepine, valproic acid, and theophylline.

(Binding Partner)

The binding partner used in the particle enhanced agglutination immunoassay according to the present invention may be any material that binds to an analyte. Examples of the binding partner include proteins, peptides, amino acids, lipids, sugars, nucleic acids, and haptens. Antibodies and antigens are typically used as binding partner, in view of their specificity and affinity. The binding partner may have any molecular weight, and may be either naturally occurring or synthesized.

(Reagents for Assay)

The reagent for use in the particle enhanced agglutination immunoassay of the present invention may have any composition. If the reagent is for use with an automated analyzer generally used in the field of clinical laboratory tests, the reagent is typically composed of two solutions: a first reagent solution (R1) containing a buffer solution; and a second reagent solution (R2) containing carrier particles which carry a binding partner or binding partners for the analyte.

(Components of Reagent for Assay)

In addition to the insoluble carrier particles carrying a binding partner or binding partners, that are the main component for reaction, the reagent for assay according to the present invention may also contain a component for buffering the ionic strength or osmotic pressure, for example, of the sample. Examples of such a component include acetic acid, citric acid, phosphoric acid, Tris, glycine, boric acid, carbonic acid, and Good's buffer, and sodium salts, potassium salts, and calcium salts thereof. The reagent for assay according to the present invention may also contain a component for enhancing agglutination. Examples of such a component include polymers such as poly(ethylene glycol), poly(vinyl pyrrolidone), and phospholipid polymer. The reagent for assay according to the present invention may also contain one or more components generally used for controlling agglutination. Examples of such a component include macromolecular substances, proteins, amino acids, sugars, metal salts, surfactants, reducing substances, and chaotropic substances. The reagent for assay according to the present invention may also contain an antifoaming substance.

(Analyzer)

The particle enhanced agglutination immunoassay of the present invention is suitable to be performed with an automated analyzer. Use of an automated analyzer reduces the total reaction time required for the immunoassay to 10 minutes or less, and allows a quick and simple determination. The automated analyzer preferably can measure the intensity of scattered light and the absorbance substantially at the same time, as is disclosed in Japanese Patent Application Laid-Open Publication No. 2013-64705.

(Scattering Angle)

The forward scattering angle in the measurement of intensity of scattered light of the present invention may have any value, and is preferably within the range of 15 to 35 degrees, more preferably within the range of 20 to 30 degrees. A scattering angle within such a range prevents excessive influences by transmitted light on a light receiver for detection of the scattered light, and is advantageous for its ability to receive the scattered light.

(Measurement of Intensity of Scattered Light)

The intensity of scattered light according to the present invention may be measured with any light source, and the light used for the measurement may have any wavelength. The light preferably has a wavelength within the visible light region, which is suitable for particle enhanced agglutination immunoassay. In particular, the wavelength is preferably within the range of 650 to 750 nm. The variation in the intensity of scattered light may be determined between any two predetermined time points. In general, higher sensitivity is provided if the time period between the two time points is longer.

The automated analyzer described above can individually determine a variation in intensity of scattered light and a variation in absorbance for a time period defined by any two time points selected between 0 and at most 1000 seconds after mixing of a sample solution containing the analyte with a solution containing insoluble carrier particles which carry a binding partner or binding partners for the analyte. If the individual variations in the intensity of scattered light and the absorbance are determined for time periods defined by two time points selected between 0 and 300 seconds after the mixing, the assay can reduce the total time of single assay (for a single sample) with the first and second reagent solutions to 10 minutes or less, and provides the benefit of the highest sample analysis speed of various commercially available automated analyzers.

(Measurement of Absorbance)

The absorbance in the present invention may be measured at any wavelength, and a suitable wavelength is within a range of ±25% of a wavelength at which the variation in intensity of scattered light is determined, preferably within a range of 550 to 900 nm, more preferably within a range of 570 to 800 nm. The wavelengths for the measurements of the absorbance and the intensity of scattered light may be either the same or different. The absorbance in the present invention may be measured either at a single wavelength or at two wavelengths consisting of a main or shorter wavelength and a sub or longer wavelength than the wavelength used in the measurement of the intensity of scattered light, within the aforementioned ranges. For example, if the intensity of scattered light is measured at a wavelength of 700 nm, the main and sub wavelengths for the measurement of the absorbance may be set within ranges of from 550 to 699 nm and from 701 to 900 nm, respectively.

The variation in the absorbance may be determined for a time period between two measurements at any two time points, and is suitably determined for a shorter period than, preferably a half or less of, the time period for which the variation in the intensity of scattered light is determined. In another embodiment, the variation in the absorbance may be preferably determined for a time period of a third or less of the time period for which the variation in the intensity of scattered light is determined. For example, if the variation in the intensity of scattered light is determined for a time period of 300 seconds, the variation in absorbance is preferably determined for a time period of 150 seconds or less, more preferably 100 seconds or less in some cases. The measurement is preferably started just after mixing the sample solution containing the analyte with the solution containing insoluble carrier particles carrying a binding partner or binding partners for the analyte.

(Variations)

The variations in values of light quantity (intensity of scattered light and absorbance) in the present invention may be determined by any method applicable to particle enhanced agglutination immunoassay, including calculation of difference, ratio, and a value per unit time for the two time points.

(Step of Correlation with an Amount of Analyte)

According to the particle enhanced agglutination immunoassay of the present invention, a sample containing a known concentration of analyte is analyzed for intensity of scattered light and absorbance to plot individual calibration curves based on the measurements. At a low concentration of analyte, the concentration is determined based on the calibration curve plotted based on the measurement of the intensity of scattered light, such that high sensitivity is achieved, and at a high concentration of analyte, the concentration is determined based on the calibration curve plotted based on the measurement of the absorbance, such that a wide dynamic range is achieved. The determination based on the absorbance provides a wide dynamic range, and allows to plot a calibration curve which covers a wider concentration range.

(Sensitivity and Dynamic Range)

The term "sensitivity" refers to a minimum measurable amount of an analyte. In general, larger variations in light quantity associated with the amount of light means higher sensitivity. In the particle enhanced agglutination immunoassay of the present invention, the high sensitivity is indicated by the high accuracy and repeatability of the measurements for the amount of the analyte at a low concentration.

The term "dynamic range" refers to a range between the lowest and highest measurable amounts of an analyte. In the particle enhanced agglutination immunoassay of the present invention, the dynamic range represents a range within which variations in light quantity proportional to the analyte concentration can be detected.

The sensitivity and dynamic range of a particle enhanced agglutination immunoassay are dependent on insoluble carrier particles which are contained in a reagent used for the assay and which carry a binding partner or binding partners to the analyte. These two characteristics are in a trade-off relation, as described above.

EXAMPLES

The present invention will now be described in more details by way of Examples, which should not be construed to limit the constitution of the present invention.

Example 1. Confirmation of Effects of the Particle Enhanced Agglutination Immunoassay According to the Present Invention Preparative Example: Preparation of a Reagent for PSA Assay 1. Preparation of the Second Reagent Solution (R2) (Solution of Antibody-Immobilized Latex)

(1) The anti-PSA monoclonal antibodies #79 and #91, and latex particles synthesized by a normal method and having an average particle size of 320 nm were separately diluted with a 20 mM glycine buffer (having a pH of 9) to prepare solutions of respective antibodies (0.7 mg/mL) and a 1% (w/w) latex solution. The solution of each antibody was mixed with an equivolume of the latex solution, and the mixture was stirred for about one hour.

(2) A blocking solution (10% BSA) was added to each of the mixtures in Step (1) in the same amount, and each mixture was stirred for about one hour.

(3) Each mixed solution in Step (2) was subjected to centrifugation to separate the supernatant, and the supernatant was then suspended in a 5 mM MOPS buffer solution (having a pH of 7.0). The resulting solution was adjusted such that the absorbance at a wavelength of 600 nm was 1.5 Abs/mL. These two solutions were then mixed in equivalent amounts to prepare a second reagent solution (R2) (solution of antibody-immobilized latex).

2. Preparation of the First Reagent Solution (R1)

A first reagent solution was prepared as 30 mM Tris-HCl buffer solution (having a pH of 8.5) containing 1 M potassium chloride and 0.1% BSA.

(Analyzer and Measurement Conditions)

Both the intensity of scattered light and the absorbance were measured in a single assay with the automated analyzer disclosed in the Japanese Patent Application Laid-Open Publication No. 2013-64705. The conditions of the measurement of the intensity of scattered light were established such that the wavelength of irradiated light was 700 nm and the scattering angle was 30 degrees. The conditions of the measurement of the absorbance were established such that the measurement was performed at two wavelengths consisting of the main wavelength of 570 nm and the sub-wavelength of 800 nm. To 8 μL of the sample containing PSA, 100 μL of R1 was added, and the mixture was stirred and then subjected to incubation for about 300 seconds at 37° C. After the incubation, 100 μL of R2 was added, and the mixture was stirred and then was subjected to incubation for about 300 seconds at 37° C. Differences in light quantity observed between selected two time points during the incubation were determined to determine variations in the intensity of scattered light and the absorbance.

(Calibration Curves and Determination of the Sample)

The measured values of the intensity of scattered light and the absorbance were respectively calibrated by spline with a PSA calibrator (available from SEKISUI MEDICAL CO., LTD.) to plot respective calibration curves. The PSA concentrations in the sample were determined based on the respective calibration curves. The concentration range of the calibration curves was selected for each measurement depending on the dynamic range under each measurement condition.

(Result 1: Sensitivity)

The variations in light quantity were determined by the immunoassay according to the present invention based on the intensity of scattered light and the absorbance. The variations were determined for a time period of 270 seconds from about 30 seconds after the addition of R2, for which the highest sensitivity is supposed in determination of PSA according to the Example. Samples containing PSA at different two concentrations (0.4 ng/mL and 1 ng/mL, respectively) were serially analyzed ten times, and the repeatability was confirmed for the measurement of the intensity of scattered light and the measurement of the absorbance (see Table 1). While the clinical cut-off value for PSA is 4 ng/mL, the measurement of the intensity of scattered light provided high sensitivity and showed high accuracy and repeatability even at a concentration of 1 ng/mL or lower.

TABLE 1

|  | Level: 0.4 ng/mL | | Level: 1 ng/mL | |
| --- | --- | --- | --- | --- |
|  | Scattered light intensity | Absorbance | Scattered light intensity | Absorbance |
|  | 0.34 | 0.29 | 1.03 | 1.24 |
|  | 0.34 | 0.54 | 0.97 | 1.36 |
|  | 0.38 | 0.58 | 0.97 | 1.27 |
|  | 0.34 | 0.49 | 1.01 | 1.22 |
|  | 0.35 | 0.68 | 1.03 | 1.31 |
|  | 0.38 | 0.78 | 1.01 | 1.31 |
|  | 0.36 | 0.85 | 1.01 | 1.41 |
|  | 0.36 | 0.90 | 1.02 | 1.44 |
|  | 0.35 | 0.49 | 1.00 | 1.56 |
|  | 0.35 | 0.73 | 0.98 | 1.39 |
| Mean | 0.36 | 0.63 | 1.00 | 1.35 |
| SD | 0.014 | 0.179 | 0.021 | 0.098 |
| CV(%) | 4.03 | 28.33 | 2.14 | 7.26 |

(Result 2: Dynamic Range)

Measurements were performed under the following conditions with different time periods for determination: the intensity of scattered light was measured for the time period between about 30 seconds after the addition of R2 (the first time point) and 270 seconds after the first time period (the second time period); the absorbance 1 was measured for the time period between about 30 seconds after the addition of R2 (the third time point (a)) and about 90 seconds after the third time point (a) (the fourth time point (a)) (condition 1 of the present invention); the absorbance 2 was measured for the time period between about 15 seconds after the addition of R2 (the third time point (b)) and about 90 seconds after the third time point (b) (the fourth time point (b)) (condition 2 of the present invention); and the absorbance 3 was measured for the time period between about 30 seconds after the addition of R2 (the third time point of the comparative example) and 270 seconds after the third time point of the comparative example (the fourth time point of the comparative example) (conventional conditions (comparative example)). Dynamic ranges of determination based on the respective measurements were then compared (see FIG. 1).

Figure 1:
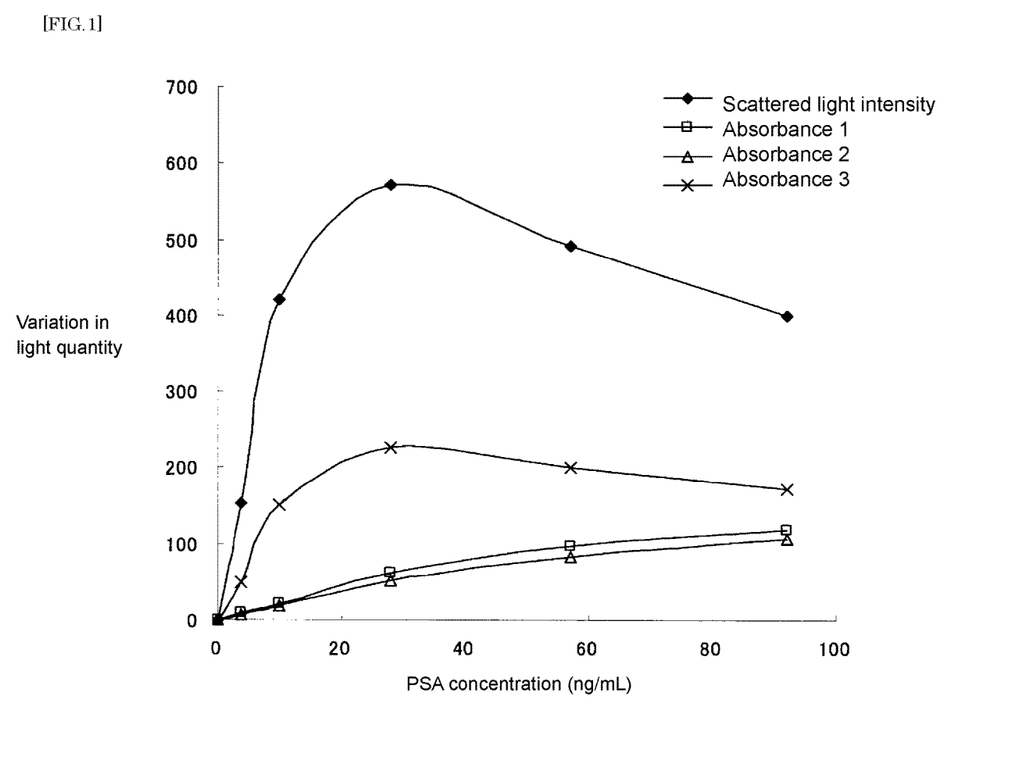
FIG. 1 is a chart for PSA concentration-dependent variations in light quantity observed under conditions of measurement of the intensity of scattered light, measurement of the absorbances in the present invention, and measurement of the absorbance in a conventional method as a comparative example.

The determination based on the measurements of the intensity of scattered light (-●-) shows a narrow dynamic range, with the peak at the PSA concentration of 25 ng/mL. At a concentration higher than 25 ng/mL, the variation in the intensity of scattered light decreases gradually. The determination based on the measurements of the absorbance 3 under conventional conditions (comparative example) (-x-) shows a similar dynamic range, but with a more modest decrease in the variation in light quantity at a high concentration range. The determination based on the measurements of absorbances 1 and 2 under the conditions of the present invention (-□- and -Δ-, respectively) shows concentration-dependent increase in light quantity even in the high concentration range. The results thus demonstrate that the present invention provides wide dynamic ranges.

(Result 3. Observation of Influences of the Prozone Effect)

Figure 2A:
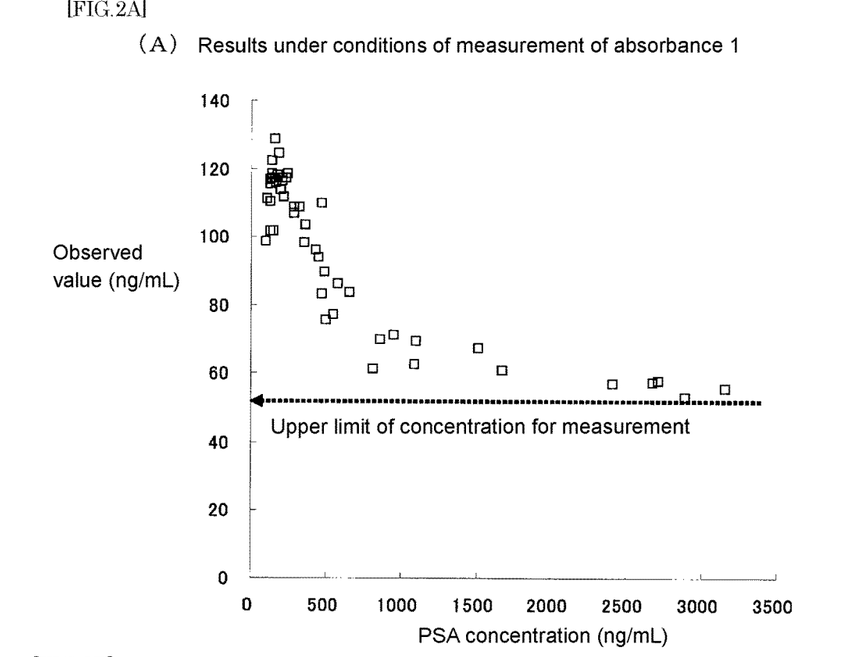
FIG. 2A is a chart for the level of decrease in measurements (under conditions of measurement of absorbance 1) due to the prozone effect observed in immunoassays of samples containing ultra-high concentrations of PSA under various conditions of measurements of absorbance in the present invention.
Figure 2B:
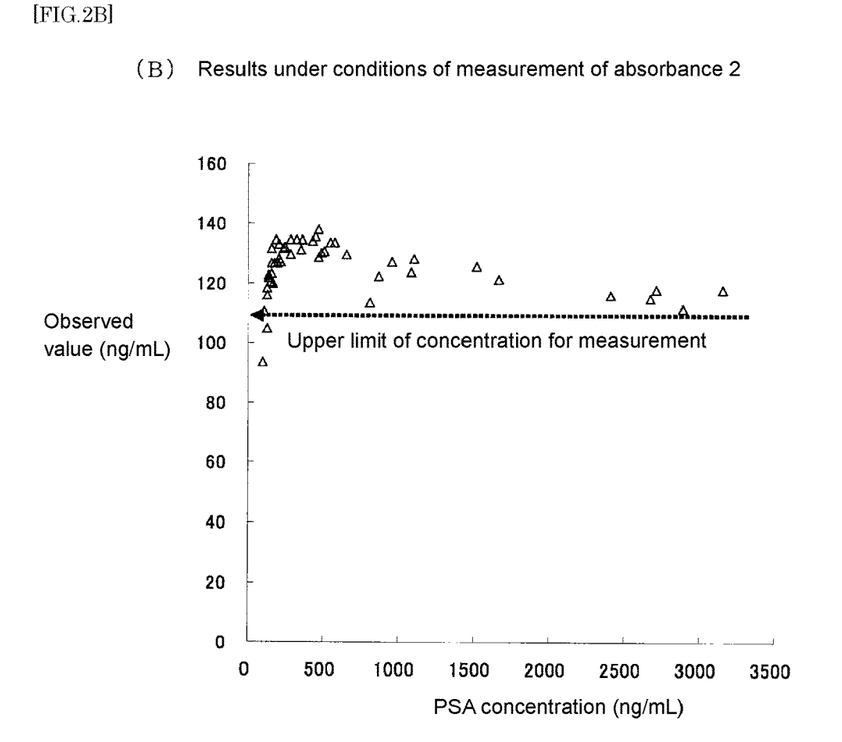
FIG. 2B is a chart for the level of decrease in measurements (under the condition of measurement of absorbance 2) due to the prozone effect observed in immunoassays of samples containing ultra-high concentrations of PSA under various conditions of measurements of absorbance in the present invention.

Samples containing PSA at concentrations exceeding the range of from 100 ng/mL to 300 ng/mL (collectively referred to as samples containing an ultra-high concentration of PSA) were analyzed under the conditions of measurements for absorbances 1 and 2 according to the present invention, to observe the prozone effect (see FIG. 2A and FIG. 2B). The prozone effect refers to a decrease in apparent measurements observed in particle enhanced agglutination immunoassay due to an excessive amount of antigen, and is a serious problem in clinical laboratory tests, because it can cause false-negative results and consequent misdiagnosis.

As a result of the analysis of the samples containing an ultra-high concentration of PSA, the determination under condition 2 showed a wider dynamic range with a more modest decrease in measurements due to the prozone effect. The results suggest that the practical upper limits of measurement under conditions of measurements for absorbances 1 and 2 are approximately 50 ng/mL (see FIG. 2A) and 100 ng/mL (see FIG. 2B), respectively, and demonstrate that the condition of measurement for the absorbance 2 allows a measurement range in a higher concentration range.

(Result 4. Correlation)

Figure 3:
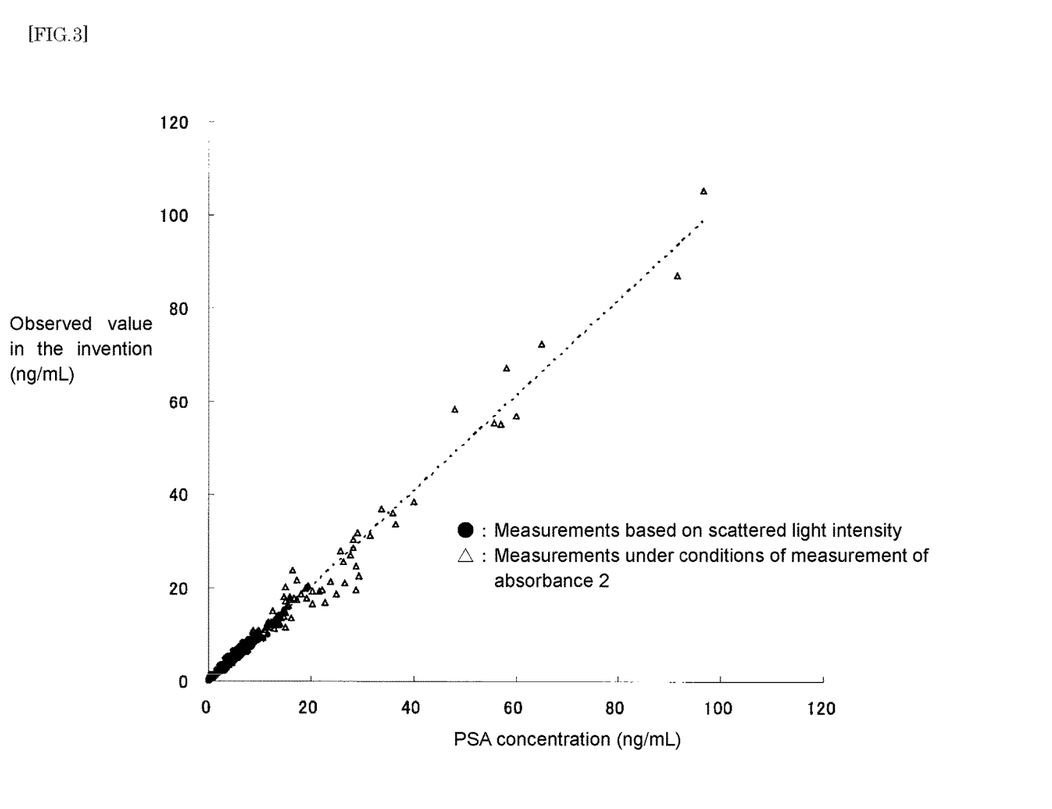
FIG. 3 is a chart for correlation observed in an immunoassays of PSA-positive samples according to the particle enhanced agglutination immunoassay of the present invention.

PSA-positive samples containing known concentrations of PSA were analyzed by the particle enhanced agglutination immunoassay according to the present invention, to confirm correlation based on measurements under the condition of measurement for the intensity of scattered light (●) and measurements under the condition of measurement for the absorbance 2 (Δ), respectively, in a low concentration range (up to 10 ng/mL) and a high concentration range (over 10.1 ng/mL) (see FIG. 3).

The results show high correlation and indicates that the present invention provides a particle enhanced agglutination immunoassay with high sensitivity and a wide dynamic range.

INDUSTRIAL APPLICABILITY

The present invention employs measurements of intensity of scattered light and absorbance in combination for a single assay. The present invention thus provides a particle enhanced agglutination immunoassay which provides higher sensitivity and a wider dynamic range than conventional assays and which reduces efforts and costs required for designing reagents for use in particle enhanced agglutination immunoassay.

REFERENCE TO DEPOSITED BIOLOGICAL MATERIALS (1) (Hybridoma #63279 producing the #79-antibody)
i) Name and address of depository institution at which the biological materials were deposited:
International Patent Organism Depositary, National Institute of Advanced Industrial Science and Technology
Tsukuba Central 6, 1-1-1 Higashi, Tsukuba, Ibaraki 305-8566, Japan
ii) Date of biological material deposit in the depository institution in i):
Feb. 19, 2010
iii) Accession number for the deposition assigned by the depository institution in i):
FERM BP-11454
(2) (Hybridoma #63291 producing the #91-antibody)
i) Name and address of depository institution at which the biological materials were deposited:
International Patent Organism Depositary, National Institute of Advanced Industrial Science and Technology
Tsukuba Central 6, 1-1-1 Higashi, Tsukuba, Ibaraki 305-8566, Japan
ii) Date of biological material deposit in the depository institution in i):
Feb. 19, 2010
iii) Accession number for the deposition assigned by the depository institution in i):
FERM BP-11455

The invention claimed is:

1. A particle enhanced agglutination immunoassay comprising the steps of:
   mixing a sample solution containing an analyte with a solution containing insoluble carrier particles carrying a binding partner or binding partners for the analyte to prepare a mixed solution;
   determining a variation (i) in intensity of light scattered from the mixed solution based on a difference in intensity of scattered light between a first and a second time point;
   determining a variation (ii) in absorbance of the mixed solution based on a difference in absorbance between a third and a fourth time point; and
      correlating the determined variation (i) in intensity of scattered light and the determined variation (ii) in absorbance with an amount of the analyte present in the sample using a calibration curve plotted based on the variation in intensity of scattered light and a calibration curve plotted based on the variation in absorbance,
   wherein at a low concentration of analyte, the concentration is determined based on the calibration curve plotted based on the measurement of the intensity of scattered light and at a high concentration of analyte, the concentration is determined based on the calibration curve plotted based on the measurement of the absorbance; and
   wherein the time period which is defined by the third and fourth time points and for which the variation (ii) is determined is shorter than the time period which is defined by the first and second time points and for which the variation (i) is determined, and the determining a variation (i) in intensity light scattered and the determining a variation (ii) in absorbance are combined in a single assay.

2. The immunoassay according to claim 1, wherein the first, second, third, and fourth time points are respectively selected between 0 and 1000 seconds after the start of preparation of the mixed solution.

3. The immunoassay according to claim 1, wherein the variations (i) and (ii) are determined at the same wavelength.

4. The immunoassay according to claim 1, wherein the variation (ii) in absorbance is determined at a wavelength within a range of ±25% of a wavelength at which the variation (i) in intensity of scattered light is determined.

5. The immunoassay according to claim 4, wherein the variation (ii) in absorbance is determined at two wavelengths consisting of main and sub-wavelengths which are shorter and longer, respectively, than the wavelength at which the variation (i) in intensity of scattered light is determined.

6. The immunoassay according to claim 1, wherein the variations (i) and (ii) are determined at a wavelength within the range of from 550 to 900 nm.

7. The immunoassay according to claim 1, wherein said calibration curves cover at least a range consisting of said low concentration of analyte and said high concentration of analyte.

* * * * *

UNITED STATES PATENT AND TRADEMARK OFFICE
CERTIFICATE OF CORRECTION

PATENT NO. : 11,536,717 B2
APPLICATION NO. : 16/256732
DATED : December 27, 2022
INVENTOR(S) : Hiroshi Takahashi et al.

It is certified that error appears in the above-identified patent and that said Letters Patent is hereby corrected as shown below:

On the Title Page

Please change:
"(73) Assignee: HITACHI HIGH-TECH CORPORATION, Tokyo (JP)"
To:
-- (73) Assignee: SEKISUI MEDICAL CO., LTD., Tokyo (JP)
  HITACHI HIGH-TECH CORPORATION, Tokyo (JP) --

Signed and Sealed this
Sixteenth Day of April, 2024

Katherine Kelly Vidal
*Director of the United States Patent and Trademark Office*